US008860948B2

(12) United States Patent
Abdulhalim et al.

(10) Patent No.: US 8,860,948 B2
(45) Date of Patent: Oct. 14, 2014

(54) HIGH RESOLUTION EXTENDED DEPTH OF FIELD OPTICAL COHERENCE TOMOGRAPHY

(75) Inventors: Ibrahim Abdulhalim, Neve Shalom (IL); Zeev Zalevsky, Rosh Ha Ayin (IL)

(73) Assignee: Ben Gurion University of the Negev Research and Development Authority Ltd.; Bar Ilan University (IL)

( * ) Notice: Subject to any disclaimer, the term of this patent is extended or adjusted under 35 U.S.C. 154(b) by 288 days.

(21) Appl. No.: 13/012,563

(22) Filed: Jan. 24, 2011

(65) Prior Publication Data
US 2011/0181888 A1 Jul. 28, 2011

Related U.S. Application Data

(60) Provisional application No. 61/282,318, filed on Jan. 22, 2010.

(51) Int. Cl.
*G01B 11/02* (2006.01)
*G01B 9/02* (2006.01)
*A61B 5/00* (2006.01)

(52) U.S. Cl.
CPC ........ *G01B 9/02056* (2013.01); *G01B 9/02091* (2013.01); *A61B 5/0066* (2013.01); *G01B 9/02005* (2013.01)
USPC .......................................... 356/497; 356/479

(58) Field of Classification Search
USPC ................................. 356/479, 497
See application file for complete search history.

(56) References Cited

U.S. PATENT DOCUMENTS

| | | | |
|---|---|---|---|
| 6,548,795 B1 | 4/2003 | Atkinson et al. | |
| 7,310,150 B2 * | 12/2007 | Guillermo et al. | ............ 356/479 |
| 7,391,520 B2 | 6/2008 | Zhou et al. | |
| 7,394,549 B2 | 7/2008 | Hendriks et al. | |
| 7,468,997 B2 | 12/2008 | Jayaraman | |
| 7,787,112 B2 * | 8/2010 | Rahn et al. | .................... 356/213 |
| 2005/0046865 A1 * | 3/2005 | Brock et al. | .................. 356/495 |
| 2006/0204861 A1 * | 9/2006 | Ben-Eliezer et al. | ............. 430/5 |

OTHER PUBLICATIONS

"Ultrahigh-resolution, high-speed, Fourier domain optical coherence tomography and methods for dispersion compensation"; Wojtkowski et al.; Optical Society of America 2004, May 31, 2004, vol. 12, No. 11, Optics Express pp. 2404-2422.
"Ultrahigh resolution optical coherence tomography imaging with a broadband superluminescent diode light source"; Ko, Tony H. et al.; Optical Society of America 2004; May 17, 2004, Vo. 12, No. 10, Optical Express, pp. 2112-2119.

(Continued)

*Primary Examiner* — Tarifur Chowdhury
*Assistant Examiner* — Jonathon Cook
(74) *Attorney, Agent, or Firm* — A.C. Entis-IP Ltd.

(57) ABSTRACT

An optical coherence tomography (OCT) imager comprising: a low coherence light source that provides light; a photosensor for imaging light; optics that directs a first portion of the light along a first optical path so that it is imaged on the photosensor and a second portion of the light along a second optical path so that it is reflected by material in the target to the photosensor where it is imaged to interfere with light from the first portion to form an interference pattern; and a mask through which light from at least one of the first and second portions of light passes that generates a relative phase perturbation between portions of light that passes through it.

23 Claims, 3 Drawing Sheets

(56) References Cited

OTHER PUBLICATIONS

"Ultrahigh-resolution full-field optical coherence tomography"; Dubois, Arnaud et al.; Optical Society of America 2004; Applied Optics, vol. 43, No. 14, May 10, 2004, pp. 2874-2883.

"Improved extended depth of focus full field spectral domain Optical Coherence Tomography"; Zlotnik, Alex et al.; Optics Communications 283 (2010), pp. 4963-4968.

"Extended focus depth for Fourier domain optical coherence microscopy", Leitgeb, R.A. et al.; Optical Society of America 2006, Optics Letters, vol. 31, No. 16, Aug. 15, 2006; pp. 2450-2452.

"All-optical axial super resolving imaging using a low-frequency binary-phase mask", Zalevsky, Zeev et al.; Optical Society of America 2006, Optics Express, vol. 14, No. 7, Apr. 3, 2006; pp. 2631-2643.

"Thin spectacles for myopia, presbyopia and astigmatism in insensitive vision"; Zalevsky, Zeev et al.; Optical Society of America 2007, Optics Express, vol. 15, No. 17, Aug. 20, 2007; pp. 10790-10803.

"Extended depth of focus contact lenses for presbyopia"; Zlotnik, Alex et al.; Optical Society of America 2009, Optics Letters, vol. 34, No. 14, Jul. 15, 2009; pp. 2219-2221.

"Competence between spatial and temporal coherence in full field optical coherence tomography and interference microscopy"; Abdulhalim, I.; Institute of Physics Publishing, Journal of Optics: Pure and Applied Optics. 8, 2006, pp. 952-958.

\* cited by examiner

HIGH RESOLUTION EXTENDED DEPTH OF FIELD OPTICAL COHERENCE TOMOGRAPHY

CROSS-REFERENCES TO RELATED APPLICATIONS

The present application claims benefit under 35 U.S.C. §119(e) of U.S. Provisional Application 61/282,318 filed Jan. 22, 2010 the entire content of which is incorporated herein by reference.

TECHNICAL FIELD

Embodiments of the invention relate to optical coherence tomographic imaging apparatus and methods that provide a three-dimensional (3D) image of a material.

BACKGROUND

An optical coherence tomography (OCT) imager uses low coherence light to image a region of interest (ROI) of a target material and provide a 3D image of the ROI. For many applications, the target materials are biological tissues, and the OCT imagers in their various configurations are operable to acquire 3D images of tissue ROIs that extend to depths of up to a few millimeters below the tissue surfaces. By way of example, OCT imagers are used to acquire 3D images of ROIs in the retina, the walls of blood vessels, and arterial occlusions.

An OCT imager typically comprises a light source, such as a superluminescent diode (SLED) or halogen lamp filtered with a monochromator, which transmits a low coherence beam of light having a relatively short coherence length. The coherence length generally ranges from a few micrometers to about a few millimeters. The beam is split to provide an imaging light beam and a reference light beam. The imaging light beam is directed to illuminate an ROI of a target material. The reference light beam is directed to illuminate a reflector.

Light from the imaging beam that is reflected by material in the ROI is combined with light from the reference beam that is reflected by the reflector to generate an interference pattern on a photosensor, which images the interference pattern. The inference pattern results from phase differences at the photosensor between the reference light and imaging light reflected by material at different locations in the ROI. The phase differences are caused by differences in path lengths from the light source to the photosensor between reference light that reaches the photosensor after reflection from the reflector and imaging light that reaches the photosensor after reflection from the different locations in the ROI. For convenience of presentation, locations of material in an ROI imaged by an OCT imager are referenced by x, y, and z-coordinates of a Cartesian coordinate system for which the z-axis is parallel to a direction of propagation in the ROI of light in the imaging beam.

Intensity of an interference pattern imaged by the photosensor that is generated by light from a narrow band of wavelengths in the imaging and reference beams represent values of a Fourier cosine integral over the z-coordinate for distribution of material in the ROI evaluated at the wavelengths in the wavelength band. Imaged interference patterns, hereinafter also referred to as an "interferograms", generated by light from different narrow wavelength bands are inverse Fourier transformed to provide a 3D image of the material in the ROI that is illuminated by the imaging beam.

For some OCT imagers, the imaging and reference beams are small cross section "pencil" beams. A Fourier interference pattern generated by the imaging and pencil beams provides information for an image of material in the ROI as a function of the z-coordinate for a small cross section "pencil shaped" region of the ROI at fixed x and y coordinates. To provide a 3D image of material in the ROI as a function of x and y coordinates as well as the z-coordinate, the imaging and reference pencil beams are scanned to provide z-axis Fourier interference patterns for each of a plurality of x and y coordinates.

"Full field OCT" imagers on the other hand use relatively large cross section imaging and reference beams to acquire 3D images of an ROI. A full field OCT imager images the imaging and reference beams on a photosensor, such as a CCD or CMOS photosensor, comprising a plurality of pixels to acquire interferograms for an ROI. Each of the interferograms provides values for a Fourier transform of material in the ROI as a function of a relatively large range of x and y coordinates, and therefore for a relatively large transverse cross section of the ROI. (A transverse cross section is a cross section in a plane perpendicular to the z-axis.) Full field OCT imagers are therefore operable to relatively rapidly acquire 3D images of a relatively large volume ROI in a target material.

The volume of the ROI is limited along the z-axis by the smaller of a coherence length of the imaging and reference beams, attenuation length of imaging light in the material of the ROI, and depth of field (DOF) of an optical system in the OCT that images imaging and reference light on the OCT photosensor. Depth of field is often the limiting factor for the z-axis dimension of the ROI and is typically determined by a tradeoff between depth of field and lateral image resolution, that is image resolution, "$\delta_{xy}$", along the x,y-axes. If $\Delta Z_{dof}$ represents magnitude of the depth of field, then assuming Gaussian optics, a constraint between lateral image resolution $\delta_{xy}$ and $\Delta Z_{dof}$ may be expressed as $$\delta_{xy} = [\lambda \Delta Z_{dof}/\pi]^{1/2}, \qquad 1)$$

from which it is seen that as depth of field increases, lateral resolution decreases. (Lateral resolution improves as $\delta_{xy}$ decreases and degrades as $\delta_{xy}$ increases. $\delta_x$ is an inverse measure of resolving power).

SUMMARY

An embodiment of the invention relates to providing a full field OCT imager that relaxes a constraint between depth of field, DOF, and lateral resolution and simultaneously provides for both an extended depth of field (EDOF) and a relatively high lateral imaging resolution.

In accordance with an embodiment of the invention, the OCT comprises an optical system having a phase mask for imaging reference and imaging light beams on a photosensor of the OCT. The phase mask is configured to moderate a rate at which the transverse cross section of a beam of light focused by the optical system to a minimum spot size on the photosensor increases from the spot size with distance from the photosensor. Optionally, the phase mask is formed as part of a lens of the optical system. In some embodiments of the invention, the phase mask is a mask which is attached to a surface of the lens. Optionally, the lens is an objective lens of the system. In an embodiment of the invention, the phase mask comprises an annular region that introduces a phase shift of about π/2 for light passing through the annular region. Optionally, the annular region has an outer circumference substantially the same as the lens with which it is associated.

There is therefore provided in accordance with an embodiment of the invention, an optical coherence tomography (OCT) imager comprising: a low coherence light source that provides light; a photosensor for imaging light; optics that directs a first portion of the light along a first optical path so that it is imaged on the photosensor and a second portion of the light along a second optical path so that it is reflected by material in the target to the photosensor where it is imaged to interfere with light from the first portion to form an interference pattern; and a mask through which light from at least one of the first and second portions of light passes that generates a relative phase perturbation between portions of light that passes through it. Optionally, light from both the first and second portions pass through the mask.

In an embodiment of the invention, the mask comprises a first annular region surrounding a central circular region, wherein the annular region generates a phase shift in light passing through the annular region relative to a phase of light that passes through the circular region. Optionally, the phase shift is between $0.20\pi \leq \phi \leq 0.80\pi$. Optionally the phase shift is substantially equal to about $0.57\pi$.

In an embodiment of the invention, the mask comprises a second annular region surrounding the first annular region. Optionally, the first annular region generates a same phase shift between light passing through the second annular region relative to light passing through the central and third annular regions. Optionally, the transmittance of the central region is about 0.25 that of the second annular region. Optionally, the transmittance of the first annular region is about 0.5 that of the second annular region.

In an embodiment of the invention, the phase perturbation introduced into light passing through the mask is a continuous function of a radial location relative to a center of the mask through which the light passes. If $\phi(r)$ represents the phase shift, its dependence on radius r is described substantially by the expression $\phi(r)=(\pi/\lambda)[r^2/(a+br^2)]$.

In an embodiment of the invention, the mask increases a depth of field of the optics relative to a depth of field that the optics would have absent the mask. Optionally, the depth of field with the mask is at least twice the depth of field without the mask. Optionally, the depth of field with the mask is at least three times the depth of field without the mask.

In an embodiment of the invention, the optics is characterized by a minimum size blur spot that is substantially the same as a minimum size blur spot without the mask. Optionally, the blur spot has a radius less than about $5\mu$. Optionally, the blur spot has a radius less than about $2.5\mu$. Optionally, the blur spot has a radius less than about $1\mu$.

In an embodiment of the invention, the second portion of light illuminates a region of the target having a cross section transverse to a direction of propagation of the light that has a diameter less than or about equal to a millimeter. Optionally, the second portion of light illuminates a region of the target having a cross section transverse to a direction of propagation of the light that has a diameter greater than a millimeter. Optionally, the second portion of light illuminates a region of the target having a cross section transverse to a direction of propagation of the light that has a diameter greater than or equal to about 2.5 millimeters. Optionally, the second portion of light illuminates a region of the target having a cross section transverse to a direction of propagation of the light that has a diameter greater than or equal to about 5 millimeter. Optionally, the second portion of light illuminates a region of the target having a cross section transverse to a direction of propagation of the light that has a diameter greater than or equal to about 10 millimeter.

In an embodiment of the invention, the OCT imager is a full field imager.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

In the following detailed description features and operation of a full field OCT imager are introduced and discussed with reference to a full field OCT imager schematically shown in FIG. 1. An embodiment of a full field OCT imager comprising a phase mask in accordance with an embodiment of the invention is described and discussed with reference to FIG. 2. A numerical example of a full field OCT imager in accordance with an embodiment of the invention is provided and features of its operation are compared to features of operation of a the full field OCT imager shown in FIG. 1.

In the discussion, unless otherwise stated, adverbs such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended.

Figure 1:
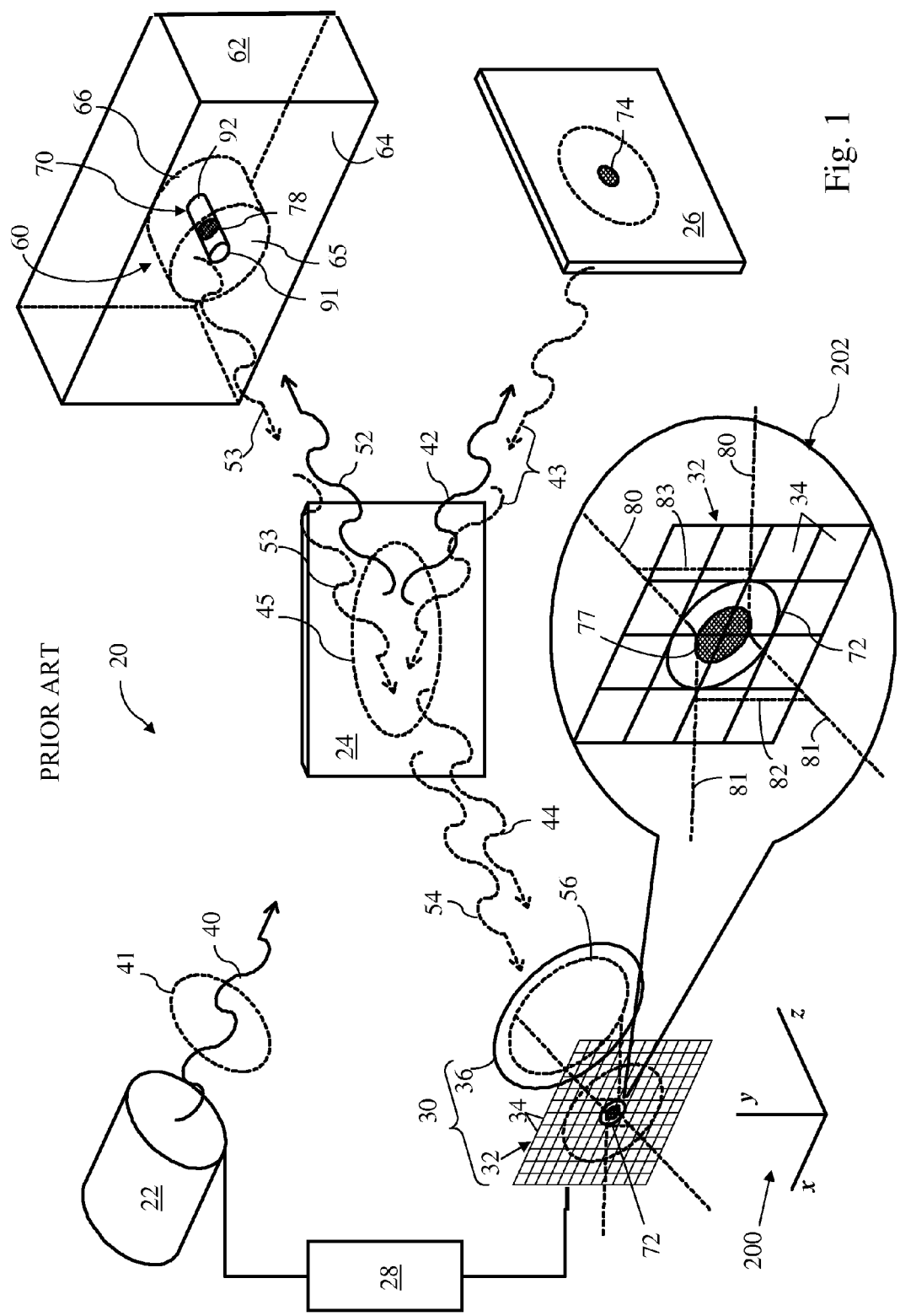
FIG. 1 schematically shows a full field OCT imager imaging a ROI of an object.

FIG. 1 schematically shows a full field OCT imager 20, also referred to hereinafter as OCT imager 20, imaging a region of interest (ROI) 60 in a target material 62, also referred to as "target 62", having an external surface 64 facing the OCT imager. Target material 62 may for example, be a biological tissue such as the retina of an eye, or a wall of a blood vessel. Target 62 is schematically shown as a rectangular solid for convenience of presentation and is indicated as being transparent to show internal features of target 62 and ROI 60, which internal features are shown in dashed lines. Locations and directions of elements and features shown in FIG. 1 are referenced for convenience to a Cartesian coordinate system 200.

OCT imager 20 optionally comprises a light source 22, a beam splitter 24, a reflector 26, and an imaging system 30. Imaging system 30 comprises a photosensor 32, such as a CCD or CMOS photosensor comprising pixels 34, and imaging optics represented by a lens 36 that images light that it receives on the photosensor. Light source 22 is optionally controllable by a controller 28 to provide a low coherence beam of light characterized by a relatively narrow wavelength band, $\Delta\lambda$, centered at any of a plurality of central wavelengths, $\lambda_c$, in a scanning range, $\lambda\Lambda$, of wavelengths. Light source 22 may comprise any suitable light generator, such as a superluminescent diode (SLED), tunable laser, or halogen lamp, and optical components such as a monochromator and/or collimator lens. The light beam provided by light source 22 is schematically represented by a wavy arrow 40. A transverse cross section of beam 40 is schematically represented by a dashed circle 41.

Light beam 40 is directed to beam splitter 24, which splits the beam into a reference beam represented by a wavy arrow 42 and an imaging beam of light represented by a wavy arrow 52. An ellipse 45 schematically represents a projection, that is a "footprint", of circular cross section 41 of light beam 40 on the beam splitter. Components of OCT 20 and coordinate system 200 are assumed to be aligned so that imaging beam 52 propagates substantially along a direction parallel to the z-axis and the reference beam propagates substantially along a direction parallel to the x-axis in the negative x-direction.

Reference beam 42 propagates from beam splitter 24 to reflector 26, which reflects light from the incident reference beam as a reflected reference beam represented by dashed wavy arrows 43 to the beam splitter. The beam splitter directs reference light, represented by dashed wavy arrow 44, from reflected reference beam 43 to imaging system 30.

Imaging beam 52 propagates from beam splitter 24 parallel to the z-axis to illuminate ROI 60 in target 62. Characteristics of light 52 and its interaction with material in target 62 determine dimensions of ROI 60. The ROI has a cross section substantially equal to that of imaging beam 52 and a length "$\Delta Z_{roi}$" along the z-axis equal to the smaller of a penetration depth of light into target 62, coherence length of imaging light 52, which is substantially equal to the coherence length of beam 40 provided by light source 22, and a DOF of imaging system 30.

In FIG. 1, ROI 60 is assumed bounded by a front surface 65 located on surface 64 and a back surface 66 inside target 62 separated along the z axis by a distance $\Delta Z_{roi}$. Light from imaging beam 52 that illuminates ROI 60 is reflected from various locations in ROI 60 by material in the ROI. The reflected imaging light, schematically represented by a dashed wavy arrows 53 is incident on beam splitter 24, which passes a portion, represented by a dashed wavy arrow 54, of the light to imaging system 30.

Lens 36 in imaging system 30 focuses imaging light 54 and reference light 44 on a region 56 of photosensor 32, where the light superposes to generate an inference pattern. Imaging light 54 having its origin in material in a small cross section tube of material in ROI 60 is imaged to a same region of pixels 34 on photosensor 32. The imaging light imaged on the region interferes with reference light reflected from a region on reflector 26 homologous with the material tube. By way of a schematic example, light from material in a material tube 70 that extends the length of ROI 60 is imaged on a region, indicated by a circle 72, of pixels 34, and interferes with reference light from a homologous region 74 on reflector 26. An inset 202 schematically shows an enlarged image of a portion of photosensor 32 that includes region 72.

Let density of mass in ROI 60 as a function of position in the ROI be represented by $\rho(x,y,z)$. Material in an "i-th" material tube, such as a material tube similar to material tube 70, may then be represented by $\rho(x_i,y_i,z)$, where coordinates $x_i$, $y_i$, are constants determined by the x, y, coordinates of the material tube, and z is variable between a minimum value $Z_{min}$ at surface 64 of target 62 and a maximum value $Z_{max}=Z_{min}+\Delta Z_{roi}$, at a depth in the target at which back surface 66 of ROI 60 is located and the ROI ends. Assume for simplicity that material in the i-th tube is imaged by lens 36 on a single pixel 34, "$p_i$", of photosensor 32. Then, if $I_I$ represents intensity of light in imaging beam 52 at surface 64 when it is incident on target 62, and reflectivity of material in the target is assumed proportional to its mass density $\rho(x,y,z)$, a complex amplitude, that is a phasor, $A_{I54}(p_i)$, representing imaging light 54 incident on pixel $p_i$ of photosensor 32 may be approximated by, $$A_{I54}(p_i)=(C_I I_I)^{1/2}[a(x_i,y_i)e^{2\pi PL_I/\lambda_c}]\int_{Z_{min}}^{Z_{max}}\rho(x_i,y_i,z)e^{i4\pi z/\lambda_c}dz. \qquad 2)$$

In the expression for $A_I(p_i)$, attenuation of imaging light 52 in target 62 is ignored for simplicity of exposition, $C_I^{1/2}$ is a proportionality constant, $a(x_i,y_i)$ is a cross sectional area of the i-th material tube, and $PL_I$ is an optical path length, which imaging light from light source 22 that reaches pixel $p_i$ travels to reach the pixel. The integral over z from $Z_{min}$ to $Z_{max}$ introduces phase differences, $i(4\pi z/\lambda)$, in imaging light 54 that reaches pixel $p_i$, which are generated by differences in z-coordinates of mass volumes $\rho(x_i,y_i,z)a(x_i,y_i)dz$ that reflect imaging light 52. As discussed below, it is these phase differences that encode information from which $\rho(x_i,y_i,z)$ is determined by OCT imager 20.

If $I_R$ represents intensity of light in reference beam 42 when it is incident on reflector 26 a phasor, $A_{R44}(p_i)$, representing reference light 44 incident on pixel $p_i$ of photosensor 32 may be approximated by, $$A_{R44}(p_i)=(C_R I_R)^{1/2}[e^{2\pi PL_R/\lambda_c}], \qquad 3)$$

where $C_R^{1/2}$ is a proportionality constant.

At pixel $p_i$, imaging and reference light 54 and 44 interfere to produce a light intensity $I(p_i,\lambda_c)$ which the pixel registers for wavelength $\lambda_c$. $I(p_i,\lambda_c)$ may be approximated by expression, $$I(p_i,\lambda_c)=C_R I_R+C_I I_I+2(C_R I_R C_I I_I)^{1/2}\int_{Z_{min}}^{Z_{max}}\rho(x_i,y_i,z)\cos(4\pi z/\lambda_c)dz, \qquad 4)$$

which may be rewritten as $$I(p_i,\kappa_c)=C_R I_R+C_I I_I+2(C_R I_R C_I I_I)^{1/2}\int_{Z_{min}}^{Z_{max}}\rho(x_i,y_i,z)\cos(\kappa_c z)dz. \qquad 5)$$

From equations 4) and 5) it is seen that $I(p_i,\lambda_c)$ is a Fourier cosine transform of mass density $\rho(x_i,y_i,z)$, that $\kappa_c=4\pi/\lambda_c=2k_c$, is a Fourier conjugate variable to z, and that $k_c$, is the wave number of the central wavelength $\lambda_c$ of light beam 40 and reference and imaging light beams 44 and 54.

To provide a 3D image of ROI 60, controller 28 controls light source 22 to generate imaging and reference beams 52 and 42 at each of a plurality of different central wavelengths $\lambda_c$, in the scanning wavelength range $\Delta\Lambda$ of light source 22 and illuminate target 62 and reflector 26 respectively with the beams. For each central wavelength $\lambda_c$, controller 28 controls imaging system 30 to acquire an interferogram (not shown) of the interference pattern generated by imaging and reference beams 54 and 44 on photosensor 32. The interferograms for the various central wavelengths $\lambda_c$ provide a discrete Fourier cosine transform of $\rho(x,y,z)$, and are processed to yield an inverse Fourier cosine transform of $\int_{Z_{min}}^{Z_{max}}\rho(x_i,y_i,z)\cos(\kappa_c z)dz$, and thereby a 3D image of $\rho(x,y,z)$ and ROI 60.

Lateral resolution, that is resolution in the x and y directions, of the interferograms acquired by OCT imager 20, and therefore for the 3D image provided by the OCT imager is a function of length, $\Delta Z_{roi}$, of ROI 60 relative to the DOF of imaging system 30.

DOF of an imaging system, such as that of lens 36 in OCT imager 20, defines a range of distances in a field of view (FOV) of the imaging system for which the system images a point source of light to a spot sufficiently small to provide acceptable image resolution. The spot is conventionally referred to as a "blur spot".

In forming an image of the point source, the system forms light that it receives from the point source into a beam of light that converges to a narrow minimum cross section waist, after which the beam diverges. The beam has a shape in the region of the waist reminiscent of an hourglass. When the point source is in focus, it is located at a distance, hereinafter an in-focus distance, from the system for which the beam waist is located at the system's imaging plane and the blur spot image of the point source has a minimum size. The minimum size blur spot is hereinafter referred to as an "in-focus" blur spot. As the point source is displaced to distances from the imaging system that are smaller or larger than the in-focus distance, the waist of the beam moves away from the imaging plane. As a result, the image of the point source is defocused, and the size of the blur spot that the system forms on its image plane with light from the point source increases, and image resolution of the system decreases.

Conventionally, the range of a DOF is defined as a range of distances, hereinafter "object distances", from a minimum, lower bound distance, to a maximum, upper bound distance for location of the light source in the system FOV, for which the radius of the blur spot is less about $\sqrt{2}$ times the radius of the in-focus blur spot. If $\delta_{xy}$ is identified with the radius of the minimum in-focus blur spot and if $r_{xy}$ is the radius of the blur spot for location of the point source at the upper and lower bounds of the DOF then $$r_{xy} = (\sqrt{2})\delta_{xy}+. \quad (6)$$

The upper and lower bound object distances correspond to upper and lower bound displacements, hereinafter referred to as "image displacements", from the image plane of the waist of the light beam that the system forms from light it receives from the light source. A distance between the lower and upper bound image displacements define a depth of focus for the system. To prevent confusion, the acronym DOF is reserved for depth of field and depth of focus will be not be referred to by an acronym but by its full name in italicized script, that is depth of focus. If a feature in the FOV of the system is imaged by the system to an image on the image plane that is M times the image of the feature, the system has a magnification M, and $$\text{depth of focus} = M^2(\text{DOF}). \quad (7)$$

Size of an optimal, focused blur spot decreases, and image resolution increases, as the f number (f#) of an imaging system, such as that of lens 36, decreases. The f# is equal to the system's focal length, f, divided by a diameter, D, of its aperture—that is f#=f/D, and is approximately equal to ½NA, where NA is a numerical aperture of the system. In terms of f#, for light having wavelength λ, radius $\delta_{xy}$ of an in-focus blur spot for a lens may be estimated by an expression, $$\delta_{xy} = 1.22\lambda f\#. \quad (8)$$

However, as the f# decreases, angles at which the imaging system bends light to an optimal in-focus blur spot increase. As a result, a rate at which the blur spot increases with image displacement from the system imaging plane increase, and depth of focus and DOF decrease. Using equations 1) and 6), displacement $\Delta Z_{dof}$ that defines magnitude of DOF may be expressed as, $$\Delta Z_{dof} = \pi\lambda(1.22 f\#)^2 \quad (9)$$

By way of example, for OCT 20, light from imaging and reference beams 54 and 44 is incident on lens 36 substantially in a circular "footprint" 56 on the lens corresponding to cross section 41 of beam 40 and is focused to photosensor 32 to form an image, represented by a circle 56, responsive to material in ROI 60 on the photosensor.

An image, indicated by a shaded circle 77, clearly shown in inset 202, of a cross section region 78, shown shaded, of material tube 70 at the center of the tube, is assumed to be in focus on the photosensor. Extreme light rays from cross section 78 that are imaged in image 77 are schematically indicated by dashed lines 80. Dashed lines 80 indicate boundaries of a light beam from cross section 78 that is imaged by lens 36 to converge to in-focus image 77. Were light in the light beam not absorbed in photosensor 32, but to continue to propagate past the photosensor surface, the light beam would begin to expand, as indicted by dashed lines 81, after passing the surface. In-focus image 77 is located at a "waist" of the light beam converging from lens 36.

Dashed lines 82 and 83 schematically represent lower and upper bounds of the depth of focus for lens 36, which are displaced on opposite sides of photosensor 32. Nearest and farthest delimiting planes in the FOV of imaging system 30 that define lower and upper bound object distances, and thereby delimit the DOF of the imaging system 30 are located in the FOV of imaging system 30 at positions that correspond to dashed lines 82 and 83. Optionally, the delimiting planes determine location of front and back surfaces 65 and 66 of ROI 60 and determine thereby length $\Delta Z_{roi}$ of the ROI. Front and back cross sections 91 and 92 of material tube 70 are optionally located on front and back surfaces 65 and 66 respectively.

Were images of front and back cross sections 91 and 92 to be imaged in-focus by imaging system 30 they would be imaged on imaging planes that are parallel to photosensor 32 and pass respectively through lines 82 and 83. However, because they are imaged on the photosensor they are imaged out of focus. Though their images, represented by circle 72, have centers that coincide with the center of image 77, their images are larger than image 77. They have enlarged radii, $r_{xy}$, because of defocusing, which may be estimated by equation 6) given above. The increase in blur spot size of outer cross sections 91 and 92 degrades lateral resolution of the interferograms acquired by OCT 20 and optionally determines limits to the length of ROI 60.

By way of a first numerical example, OCT imager 20 optionally operates in a wavelength range $\Delta\Lambda$ for which $500 \leq \lambda_c \leq 600$ nm (nanometers) and light beams 44 and 54 have bandwidth $\Delta\lambda=2$ nm Optionally, lens 36 has a focal length f=125 mm (millimeters), diameter D=22.8 mm and f#=5.48 (NA≈0.09). Target 62 is optionally located 60 mm from lens 36 and the OCT imager has a magnification factor of about 5.6.

For a representative wavelength $\lambda_c=550$ nm, the above values, and using equation 8), a minimum focused blur spot has a radius $\delta_{xy} \approx 3.7\mu$ (micrometers). From equation 9), $\Delta Z_{dof} \approx 77\mu$ and from equation 6) $r_{xy} \approx 5.2\mu$.

By way of a second numerical example, assume that imaging system 30 has an f# equal to about 1 (NA≈0.5). Then OCT 20 has a sub-micron blur spot radius $\delta_{xy} \approx 0.67\mu$ providing submicron imaging resolution suitable for imaging cells and parts of cells. However, for the given resolution, the OCT 20 imager has a shortened DOF equal to about 2.6μ.

Figure 2:
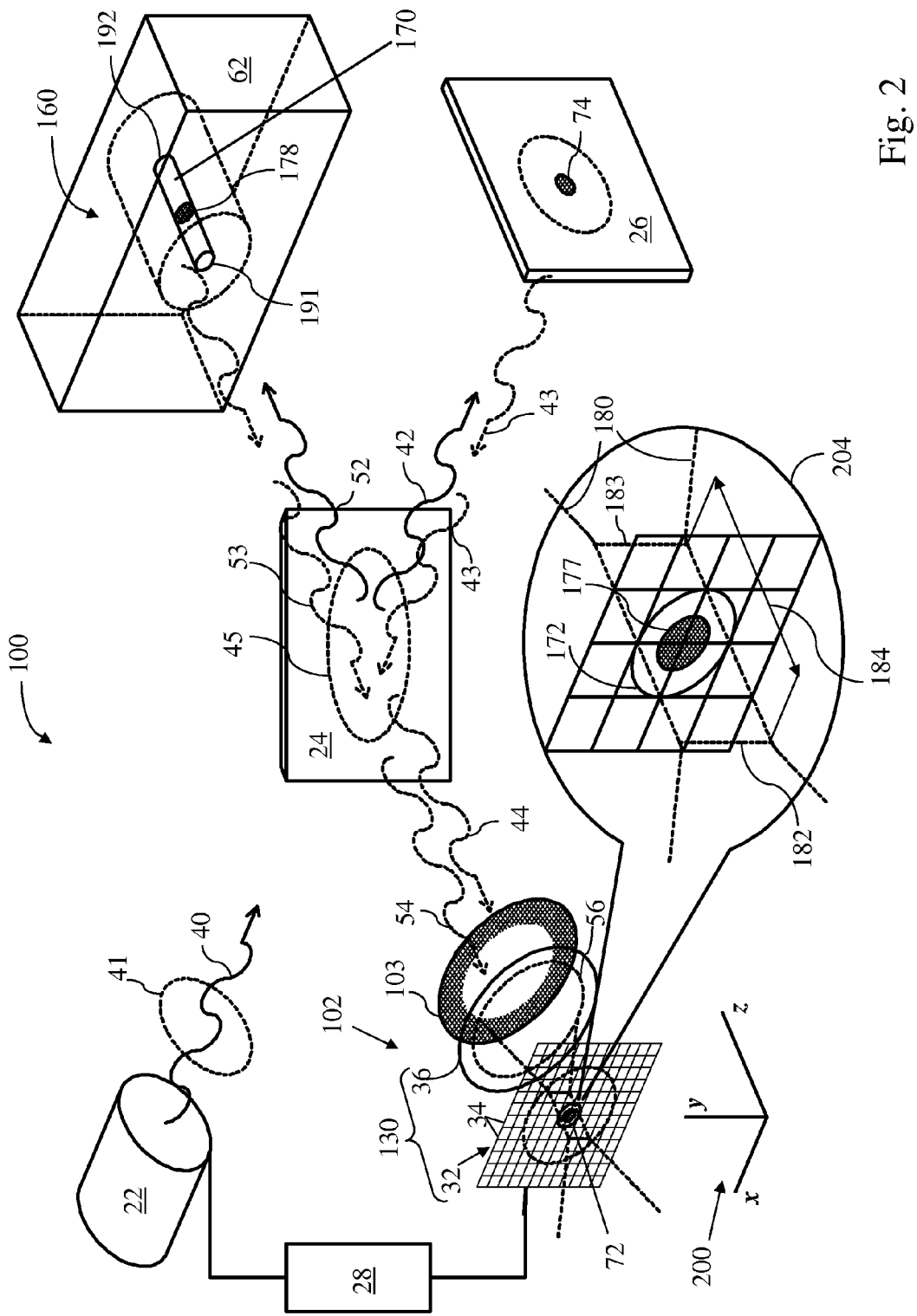
FIG. 2 schematically shows full field OCT imager imaging the ROI of the object shown in FIG. 1, in accordance with an embodiment of the invention.

FIG. 2 schematically shows an OCT imager 100 comprising a phase mask 102, which relaxes a constraint between DOF and lateral resolution $\delta_{xy}$, and simultaneously provides for both an extended depth of field (EDOF) and a relatively high lateral imaging resolution, in accordance with an embodiment of the invention. In FIG. 2 OCT imager 100 is schematically shown imaging an ROI 160.

OCT imager 100 optionally comprises the same components as OCT imager 20 except that in place of imaging system 30 it comprises an imaging system 130. Imaging system 130 optionally comprises the same components that are comprised in imaging system 30, but in addition, comprises phase mask 102 through which imaging light 54 and reference light 44 pass on their way to being imaged on photosensor 32. Phase mask 102 is configured to introduce a phase perturbation in at least a portion of the imaging and reference light that passes through the phase mask. The phase perturbation operates to extend the DOF of OCT 100 relative to that provided by OCT imager 20.

In an embodiment of the invention, phase mask 102 comprises an annular region 103 that introduces a phase shift perturbation in that portion of imaging light 54 and reference light 44 that passes through the annular region. Optionally, the annular region has an outer radius substantially the same as that of an entrance aperture of imaging system 130 and an inner radius greater than about half the radius of the entrance aperture. Optionally, the inner radius is greater than or about equal to about 0.70 times the outer radius. In some embodiments of the invention, the inner radius is greater than or about equal to 0.80 times the outer radius. In an embodiment of the invention, the annular region introduces a phase shift perturbation $\phi$ into imaging and reference light that satisfies a constraint $0.20\pi \leq \phi \leq 0.80\pi$. Optionally, the phase shift is substantially equal to about $0.5\pi$.

In some embodiments of the invention, as shown in OCT imager 100 phase mask 102 is separate from other components in the imaging system. In some embodiments of the invention a phase mask is an integral part of another component in the imaging system. For example, a phase mask may be integrally formed as part of lens 36.

As the discussion above of operation of OCT imager 20 clearly shows, information acquired by an OCT imager is coded in the phase interference of imaging light with reference light. It would therefore appear that introducing phase perturbations in portions of the interfering light would substantially degrade operation of an OCT imager. However, surprisingly, a phase mask configured in accordance with an embodiment of the invention operates to substantially increase DOF of an OCT imager without substantially degrading interference data that the OCT imager acquires.

For example, a phase mask such as phase mask 102 may operate to provide OCT imager 100 with an extended DOF relative to that of OCT imager 20 by substantially extending a narrow waist of a light beam that lens 36 converges to photosensor 32. By extending the narrow waist the phase mask moderates a rate at which a radius of a blur spot increases with displacement of its in-focus image from photosensor 32.

FIG. 2 schematically shows light rays, represented by dashed lines 180, from a material tube 170 that imaging system 130 focuses to photosensor 32. The light rays indicate boundaries of a light beam generated by lens 30 from light that imaging system 130 receives from a central cross section 178 of material tube 170 that is imaged by lens 32 to converge to an in-focus image 177 of cross section 178 on the photosensor. An enlarged image of a portion of photosensor 32 is schematically shown in an inset 204. The image shows that phase mask 102 has shaped the light beam from cross section 178 to have an elongated waist 184 bounded by lower and upper bounds represented by lines 182 and 183. Lower and upper bounds 182 and 183 delimit an extended depth of focus for OCT 100, in accordance with an embodiment of the invention. As a result of the elongated depth of focus, OCT imager 100 is characterized by an extended DOF and the OCT imager is able to acquire images for ROI 160 having a length substantially longer than that of ROI 60 (FIG. 1) without sacrificing image resolution. For example, a large circle 172 schematically indicates images of front and back cross sections 191 and 192 of material tube 170. Because of the extended DOF that phase mask 102 provides, ROI 160 and material tube 170 may be substantially longer than ROI 60 and material tube 70, while the size of images 170 of front and back cross sections 191 and 192 is the same as that of front and back cross sections 91 and 92 of material tube 70.

In some embodiments of the invention phase mask 102 provides an extended DOF for OCT imager 100 that is at least twice as long as that of the DOF that characterizes OCT imager 20.

By way of a numerical example, in an embodiment of the invention, phase mask 102 for a full field OCT imager similar to OCT imager 100 was configured for the dimensions of lens 36 given above in the first numerical example for OCT imager 20, and region 103 had an outer radius substantially equal to 11.4 mm and an inner radius substantially equal to about 8 mm. The phase mask introduced a phase perturbation of about $\pi/4$ for light passing through region 103 and provided an extended DOF for OCT imager 100 that was about twice that of OCT 20 while maintaining blur spot radius $\delta_{xy} \approx 3.7\mu$.

By way of another example, OCT 100 can be configured to provide a same DOF as that of OCT 20 but an image characterized by a substantially improved blur spot radius $\delta_{xy}$ and therefore resolution, by configuring imaging system 130 to have an f# about equal to about 2.8 (NA≈0.18). The OCT imager will then have a blur spot radius $\delta_{xy}$ equal to about $1.9\mu$ (for $\lambda=550$ nm). Without a phase mask in accordance with an embodiment of the invention, the DOF for the OCT imager would be about $20\mu$. With a phase mask, in accordance with an embodiment of the invention, the DOF can be extended by a factor of three to a length of about $60\mu$ without substantially increasing the blur spot radius.

Figure 3:
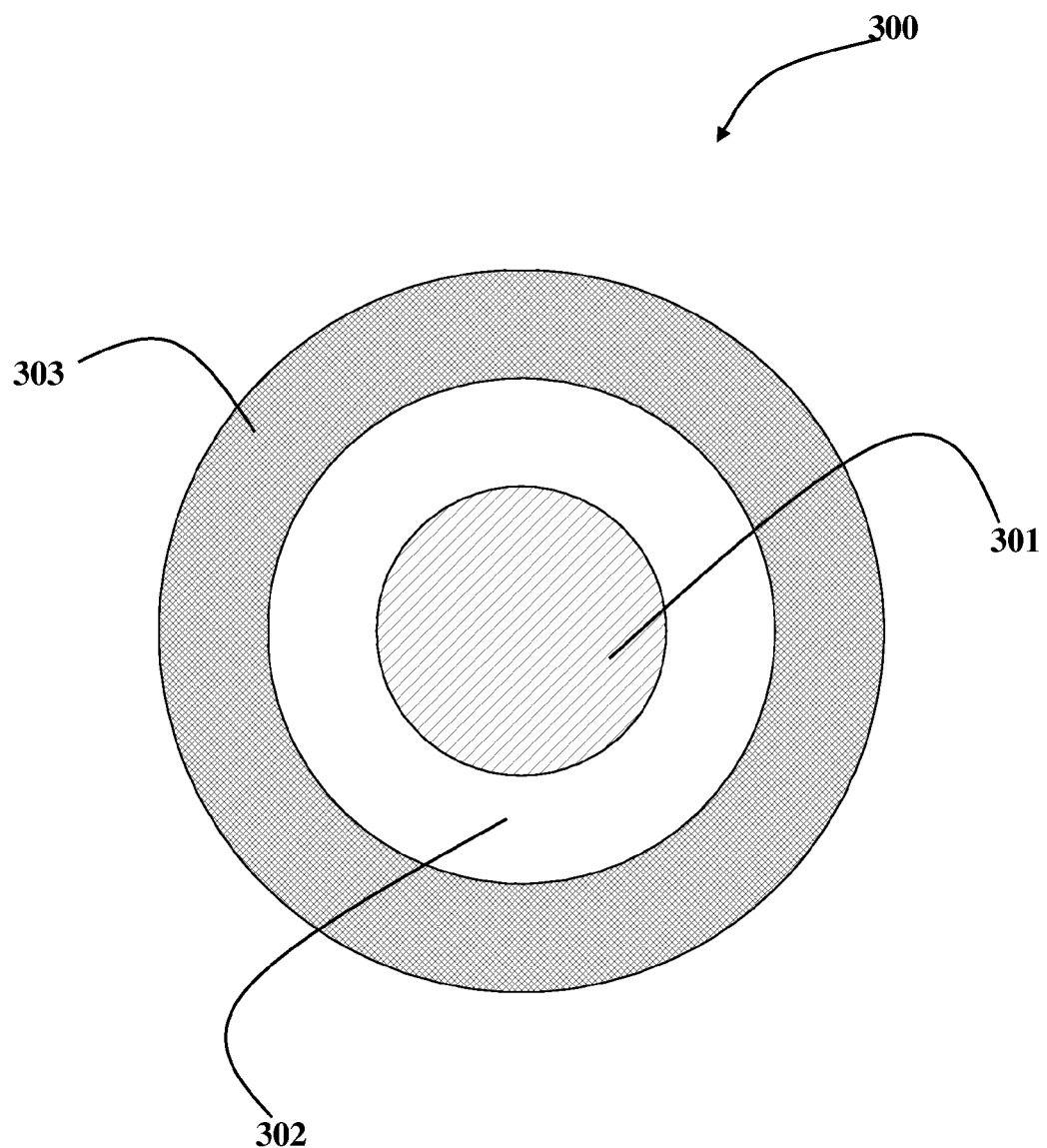
FIG. 3 schematically shows a mask for introducing a perturbation into light that provides an interferogram, in accordance with an embodiment of the invention.

A phase mask similar to a phase mask 300, which is not only a phase mask but a phase and amplitude mask, schematically shown in FIG. 3 may be suitable to provide the threefold increase in DOF. Phase mask 300 comprises a central circular region, 301 surrounded by two concentric annular regions 302 and 303 respectively. Region 302 introduces a phase shift of about $\pi/2$ into light passing through the region. The other regions do not phase shift light that passes through the regions. However regions 301, 302 and 303, amplitude modulate light that passes through them and regions 301 and 302 have transmittances of about 0.25 and about 0.5 respectively of a transmittance of region 303.

By way of yet another example, a mask similar to mask 300 may be used in accordance with an embodiment of the invention to provide a relatively large DOF having submicron resolution by adding the mask to an OCT imager having specifications similar to that given for second numerical example for an OCT imager similar to that of OCT imager 20 having an f# equal to about 1. The OCT imager configured with the phase mask would have $\delta_{xy} \approx 0.67\mu$ and a DOF equal to about $7.8\mu$.

Another mask that may be used in the practice of the invention to increase the DOF of an OCT imager by a factor of three is a mask that introduces a phase perturbation "$\phi(r)$" to light passing through the mask that is a continuous function of radius "r" of the mask. In an embodiment of the invention, $$\phi(r)=(\pi/\lambda)[r^2/(a+br^2)]. \quad\quad 10)$$

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A full field optical coherence tomography (OCT) imager comprising:
    a low coherence light source configured to provide light for full field illumination of a target;
    a photosensor for imaging light;
    optics that directs a first portion of the light along a first optical path so that it is imaged on the photosensor and a second portion of the light along a second optical path so that it is reflected by material in the target to the photosensor where it is imaged to interfere with light from the first portion to form an interference pattern;
    a mask through which light from at least one of the first and second portions of light passes that generates a relative phase perturbation between portions of light that pass through it;
    wherein interfering light from the first portion that passes through the mask, and/or light from the second portion that is reflected from a same region of the target and passes through the mask, and is imaged to substantially a same region of the photosensor, comprises light having a phase difference generated by passing through the mask.

2. An OCT imager according to claim 1, wherein light from both the first and second portions pass through the mask.

3. An OCT imager according to claim 1, wherein the mask comprises a first annular region surrounding a central circular region, wherein the annular region generates a phase shift in light passing through the annular region relative to a phase of light that passes through the circular region.

4. An OCT imager according to claim 3, wherein the phase shift is between $0.20\pi \leq \phi \leq 0.80\pi$.

5. An OCT imager according to claim 4, wherein the phase shift is substantially equal to about $0.5\pi$.

6. An OCT imager in accordance with claim 3 wherein the mask comprises a second annular region surrounding the first annular region.

7. An OCT imager according to claim 6, wherein the first annular region generates a same phase shift between light passing through the first annular region relative to light passing through the central and second annular regions.

8. An OCT imager according to claim 7, wherein the central region is characterized by a transmittance equal to about 0.25 that of the second annular region.

9. An OCT imager according to claim 7, wherein the first annular region is characterized by a transmittance equal to about 0.5 that of the second annular region.

10. An OCT imager according to claim 1, wherein the phase perturbation introduced into light passing through the mask is a continuous function of a radial location relative to a center of the mask through which the light passes.

11. An OCT imager according to claim 10 wherein if $\phi(r)$ represents the phase shift its dependence on radius r is described substantially by the expression $\phi(r)=(\pi/\lambda)[r^2/(a+br^2)]$, where a and b are constants independent of r.

12. An OCT imager according to claim 1, wherein the mask increases a depth of field of the optics relative to a depth of field that the optics would have absent the mask.

13. An OCT imager according to claim 12, wherein the depth of field with the mask is at least twice the depth of field without the mask.

14. An OCT imager according to claim 12, wherein the depth of field with the mask is at least three times the depth of field without the mask.

15. An OCT imager according to claim 12, wherein the optics is characterized by a minimum size blur spot that is substantially the same as a minimum size blur spot without the mask.

16. An OCT imager according to claim 15, wherein the blur spot has a radius less than about $5\mu$.

17. An OCT imager according to claim 16, wherein the blur spot has a radius less than about $2.5\mu$.

18. An OCT imager according to claim 17, wherein the blur spot has a radius less than about $1\mu$.

19. An OCT imager according to claim 1, wherein the second portion of light illuminates a region of the target having a cross section transverse to a direction of propagation of the light that has a diameter less than or about equal to a millimeter.

20. An OCT imager according to claim 1, wherein the second portion of light illuminates a region of the target having a cross section transverse to a direction of propagation of the light that has a diameter greater than a millimeter.

21. An OCT imager according to claim 20, wherein the second portion of light illuminates a region of the target having a cross section transverse to a direction of propagation of the light that has a diameter greater than or equal to about 2.5 millimeter.

22. An OCT imager according to claim 21, wherein the second portion of light illuminates a region of the target having a cross section transverse to a direction of propagation of the light that has a diameter greater than or equal to about 5 millimeter.

23. An OCT imager according to claim 22, wherein the second portion of light illuminates a region of the target having a cross section transverse to a direction of propagation of the light that has a diameter greater than or equal to about 10 millimeter.

* * * * *